United States Patent [19]

Fleischmann

[11] Patent Number: 5,030,716

[45] Date of Patent: Jul. 9, 1991

[54] METHODS AND COMPOSITIONS EMPLOYING INTERFERON-GAMMA

[75] Inventor: W. Robert Fleischmann, Galveston, Tex.

[73] Assignee: Board of Regents, The University of Texas System, Austin, Tex.

[21] Appl. No.: 523,031

[22] Filed: May 14, 1990

Related U.S. Application Data

[62] Division of Ser. No. 916,008, Oct. 6, 1986, Pat. No. 4,950,470.

[51] Int. Cl.$^5$ .................... C07K 15/26; A61K 37/66
[52] U.S. Cl. .................................. 530/351; 424/85.5
[58] Field of Search ....................... 530/351; 424/85.5

[56] References Cited

PUBLICATIONS

Lundblad, et al., "Chemical Reagents for Protein Modifications", vol. 1, CRC Press, Inc., Boca Raton, Fl., pp. 55–61.

Primary Examiner—Margaret Moskowitz
Assistant Examiner—R. Keith Baker
Attorney, Agent, or Firm—Arnold, White & Durkee

[57] ABSTRACT

The present disclosure is directed to improved pharmaceutical compositions employing interferon-gamma which have been treated to remove interferon-gamma inhibitory activity associated with such preparations. In addition, the present disclosure details treatment protocols, including the elevation of patient body temperature and the use of combined or sequential interferon-gamma treatments, to enhance interferon-gamma efficacy and reduce the resistance associated with interferon-alpha and/or beta therapy.

6 Claims, 6 Drawing Sheets

METHODS AND COMPOSITIONS EMPLOYING INTERFERON-GAMMA

The Government may own certain rights in the present invention pursuant to USPHS Grant Ca26575 and ACS grant IFN-3.

This is a divisional of copending application Ser. No. 07/916,008, filed Oct. 6, 1986, now U.S. Pat. No. 4,950,470.

BACKGROUND OF THE INVENTION

The Government may own certain rights in the present invention pursuant to USPHS Grant Ca26475 and ACS grant IFN-3.

1. Field of the Invention

The present invention is directed to improved methods and compositions which incorporate interferon gamma for the treatment of viral infections and neoplastic disease. In particular, the present invention is directed to an improved interferon gamma preparation which exhibits a greatly enhanced activity over previously available preparation and, further, the use of interferon gamma preparations in treatment protocols designed to provide maximal antitumor and antiviral activity.

2. Description of the Related Art

Interferons (IFN-alpha, IFN-beta and IFN-gamma) are natural host proteins which have antiviral, immunoregulatory and antiproliferative activity. A number of clinical trials have examined interferons in order to assess their clinical potential. (For a review, see Borden (1983), "Interferons: In Pursuit of the Promise," in: 13th Int'l. Congress, Part E, Cancer Management, Mirand et al., eds., Alan R. Liss, N.Y., 287-296). Unfortunately, while certain interferons have demonstrated real promise for the control of certain types of cancer, for example, the use of IFN-alpha in hairy cell leukemia, they have for the most part been limited in their effectiveness and have not been found to be highly potent against most types of cancer tested. Further, interferon therapy has a number of important side efforts, in particular, bone marrow suppression. Therefore, a major challenge facing medical science is to increase the antitumor activity of the interferons while reducing or moderating their side effects.

One problem which has been identified with respect to IFN-gamma treatment is the apparent association of IFN-gamma preparations, including recombinantly-produced preparations, with an inhibitory activity. This IFN-gamma inhibitory activity was first identified and discussed by Fleischmann et al. (1979), *Infec. and Immun.*, 26(3): 949-55, where it was observed that an inhibitor could be partially purified from IFN-gamma preparations, which inhibitor demonstrated a profound ability to block the antiviral activity of up to 400 units of interferon. Further studies by Lefkowitz et al. (*Jrnl. Interferon. Res.* (1985), Vol. 5: 85-99 and Vol. 5: 101-110) have demonstrated the existence of this inhibitory activity in a variety of interferon gamma preparations. Thus, an important step in maximizing the clinical usefulness of IFN-gamma would be to provide IFN-gamma preparations wherein this inhibitory activity has been minimized or removed altogether.

Further problems previously associated with IFN therapy has been the development of viral and tumor resistance to IFN-alpha and beta therapy that results in an apparent decreased sensitivity of these clinical targets to treatment. Attempts to alleviate this problem through increased dosages of IFN's have merely exacerbated the bone marrow toxicities associated in the IFN therapy. Accordingly, treatment regimens are needed which would provide both a decrease in the occurrence of IFN associated resistance and myelospression while providing an enhanced IFN activity.

SUMMARY OF THE INVENTION

The present invention is directed to solving many of the problems previously associated with IFN therapy in general, and with IFN-gamma therapy in particular. The present disclosure focuses on this challenge by providing a means for removing an inhibitor of IFN action from IFN-gamma preparations to maximize IFN-gamma antiviral and antiproliferative activity.

In other aspects, combined interferon treatment (IFN-gamma plus either IFN-alpha or IFN-beta) in various treatment protocols are evaluated as a means of maximizing interferon activity. Moreover, the usefulness of combining hyperthermic treatment with IFN-gamma therapy is demonstrated to provide a synergistic effect on IFN-gamma activity.

Accordingly, the present invention provides a method for enhancing the effectiveness of an interferon gamma preparation which includes treating an aqueous preparation which contains interferon gamma with a reducing agent to reduce disulfide moieties to sulfhydryl moieties, followed by treating the reduced preparation with an acylating agent to acylate the reduced sulfhydryl moieties and thereby inhibit the formation of disulfide bonds in the preparation. Any reducing agent which is capable of reducing disulfide moieties to sulfhydryl moieties may be utilized, however, in a preferred embodiment, the reducing agents found to be particularly suitable are 2-mercaptoethanol or dithiothreitol. These agents have the advantage of long shelf life and no reacting groups by which side reactions might occur with proteins in the IFN-gamma preparation being reduced.

The acylating agent of choice is iodoacetate in that this agent is a relatively mild acylator that will not react with few structures other than the reduced sulfhydryl groups (the epislon amino group of lysine, for example). However, those at skill in the art will recognize that numerous other acylating agents may be employed to inhibit the reformation of disulfide bonds in the reduced preparation, for example, other keto alkyl halides such as bromoacetic acid and chloroacetic acid, and their corresponding amides such as chloroacetamide.

A method is also provided for the treatment of neoplastic disease in a patient which includes elevating the body temperature of the patient to a temperature between about 37.3 and about 40.5 degrees centigrade and administering to the patient a pharmaceutically acceptable preparation which includes an effective dose of interferon gamma. In a preferred embodiment, the patient's body temperature is elevated to approximately 39.4 degrees centigrade to achieve a maximal hyperthermia-induced enhancement of IFN-gamma activity.

In further aspects, a method is provided for enhancing the effectiveness of alpha, beta or combined alpha/beta interferon therapy in a patient undergoing such therapy which includes administering to the patient a pharmaceutically acceptable preparation which includes an effective amount of interferon gamma.

Thus, a reduction in the incidence of interferon-associated resistance may be achieved by sequentially administering to such a patient a first and a second pharmaceutically acceptable interferon containing preparation wherein the first interferon preparation includes an effective dose of interferon alpha or beta and the second interferon preparation includes an effective amount of interferon gamma.

In a preferred embodiment, interferon gamma containing preparations are administered for about 1 to about 3 days and withdrawn for about 1 to about 3 days, while the patient is maintained at a selected dosage of interferon alpha, beta or alpha/beta. Alternatively, the patient may be treated with this interferon alpha and/or beta containing preparation only those days on which the interferon gamma containing preparation has been withdrawn. Through utilization of these treatment protocols, the resistance which is associated with interferon alpha and/or beta therapy is reversed through the action of the interferon gamma containing preparation.

DETAILED DESCRIPTION OF THE PREFERRED EMBODIMENTS

Figure 1:
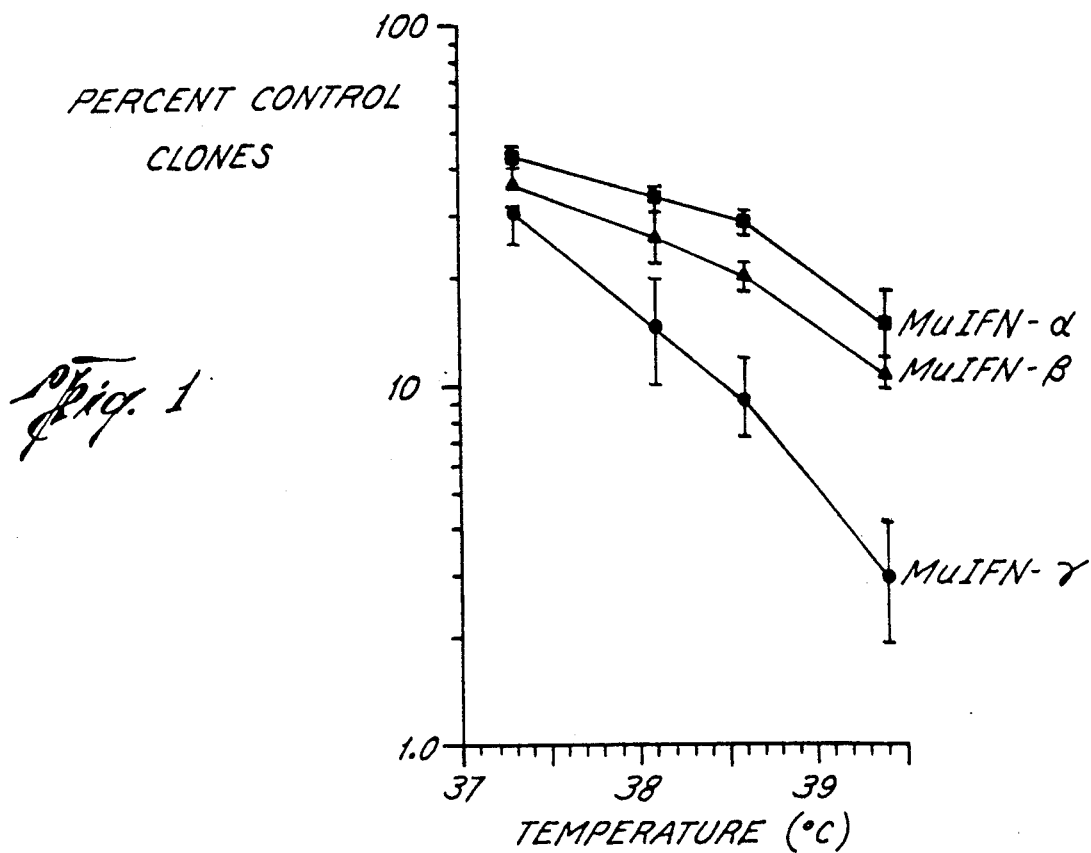
FIG. 1. Effect of elevated temperatures on the antiproliferative activities of interferons. Log phase mouse B-16 melanoma cells were plated at 300 cells/35-mm Petri dish into growth medium, 3000 units of IFN-alpha/ml, 3000 units of IFN-beta/ml, or 30 units of IFN-gamma/ml. Replicate sets of plates were incubated for 6 days at 37.3, 38.1, 38.6, and 39.4° C. in Napco Model 5300 incubators. Temperatures were determined using an ASTM No. 91C (Fisher Scientific) thermometer. The clones were stained with 1% crystal violet in 20% methanol (w/v). Experiments were performed in triplicate. Control plates had the following cloning efficiencies: 64% at 37.3° C., 57% at 38.1° C., 55% at 38.6° C., and 48% at 39.4° C. The data were plotted as the percentage of control clones at the indicated temperatures. Points, mean; bars, SE.

Interferons are a complex set of naturally produced proteins and glycoproteins which have been recognized and named for their ability to inhibit virus replication through a cell-mediated process. Three antigenic types of interferon have been recognized: IFN-alpha, also known as leukocyte interferon; IFN-beta, also known as fibroblast interferon; and IFN-gamma, also referred to as immune interferon. IFN-alpha and IFN-beta have been shown to have some homology at the molecular level and to have many similar physiochemical and biological properties. They have also been referred to as type I interferons. IFN-gamma has been shown to have no direct homology with IFN-alpha and IFN-beta at the molecular level, to activate cells more slowly than IFN-alpha and IFN-beta, and to have more potent antiproliferative and immunoregulatory activities than IFN-alpha and IFN-beta. IFN-gamma has also been referred to as type II interferon.

In addition to their antiviral activity, interferons also have antiproliferative and immunoregulatory activities which, in animal systems, contribute to a potent antitumor effect. The applicability of this antitumor effect of interferon to man has been recently confirmed with respect to Hairy cell leukemia.

The present disclosure is directed to a number of useful methods and compositions which incorporate type II Interferon (IFN-gamma) in a manner which should prove useful in the treatment of viral and neoplastic diseases. Although the present disclosure is limited to in vitro exemplary matter, it is believed that the following examples and experiments are conducted in systems which have attained a level of acceptance in the art to demonstrate correspondence to the in vivo activity. Moreover, although many of the hereinafter described examples incorporate murine interferons, examples are also included which employ their human counterparts. Therefore, it is believed by the present inventors that there is a general correspondence of phenomena between the murine and human interferons. This correspondence is generally accepted by those knowledgeable in the art.

A. Studies on the Synergistic Interactions of Interferons Employed in Combination Studies on the biological differences between type I and type II interferons have demonstrated that a potentiation of both antiviral and antiproliferative efficacy is observed when combined preparations of type I and type II interferons are employed. Potentiation was originally observed in the mouse system as a greater than additive enhancement of the antiviral action of interferon. Subsequent studies have demonstrated that type II interferon (IFN-gamma) interacts synergistically with either of the type I interferons (IFN-alpha or IFN-beta) to potentiate interferons antiviral activity, but that the two type I interferons interact with each other only additively.

Moreover it can be demonstrated that combination interferon therapy with murine IFN-gamma+murine IFN-alpha/beta has the ability to potentiate interferon's in vivo antitumor effect in the mouse tumor model system using a lymphocytic leukemia (P388). Experimental results provide convincing evidence that combinations of the type I+type II interferons potentiated their antitumor activity.

These observations have been extended to show potentiation of the direct antiproliferative aspect of interferon's antitumor activity. In a clonogenic assay of mouse B-16 melanoma cells in the presence of interferon gamma, interferon-alpha/beta, or the combination of interferon gamma plus interferon alpha/beta, a potentiation of the direct antiproliferative activity was shown to be dependent on the concentrations of both IFN-gamma and IFN-alpha/beta, with potentiation levels increasing dramatically as the interferon concentrations were increased. The clonogenic assay is a well accepted assay for determining the antiproliferative activity of a particular agent. The maximum level of potentiation observed was 214-fold at the highest interferon concentrations employed; however, the data suggested that the potentiation level was not yet approaching a peak value. These results suggest that potentiation of interferons direct antiproliferative effect may increase without limit as the concentrations of the interacting interferons increase. Additional studies have shown that IFN-gamma interacts synergistically with either IFN-alpha or IFN-beta to potentiate their direct antiproliferative activity but that IFN-alpha and IFN-beta, as in the situation of their antiviral activity, interact only additively.

Additional studies have employed a recombinant DNA-derived IFN-gamma and antibodies to IFN-gamma to study the role of IFN-gamma in the potentiation interaction. The results of this studies conclusively demonstrated that the potentiation factor in IFN-gamma preparations was interferon gamma itself.

Other studies have been employed extending the foregoing to the human system using both highly purified and natural human IFN-gamma and recombinant DNA-derived IFN-gamma preparations. The data show that potentiation works in an identical fashion in both the mouse and human systems, indicating that the studies in the mouse system have direct applicability to the clinical setting.

One particular concern was whether combination interferon therapy, with its attendant potentiation of interferons antiproliferative activity, would be too potent in its action against non-malignant cells to be successfully employed in the clinic. However, studies employing paired sets of malignant and non-malignant cells of epidermal origin have addressed this concern and found that interferon treatment, particularly combination interferon treatment, was markedly more potent against malignant cells. While more study is required, the data suggests that the future for combination therapy is promising.

B. Studies on the Enhancing Effect of Elevated Temperature on the Antiproliferative Activity of Interferons The previously described studies on the synergistic interactions of type I and type II interferons suggested the possibility that other components of the host defense system might interact with interferon to give an enhanced effect. Since fever is one such host defense system, it was felt that an "artificially induced" hyperthermia may provide a potentiation of IFN-gamma action as well. Thus studies were undertaken to examine the effects of elevated temperature on all three interferon types, alone and in combination. It was determined that the antiproliferative activities of all three interferons were enhanced by incubating the treated cells at the elevated temperatures. An elevated temperature of 39.4° C. was chosen because it is physiologically attainable in the clinical setting through the use of, for example, a heat blanket or concurrent ultrasound therapy. These studies demonstrated a more dramatic enhancing effect on the antiproliferative activity of IFN-gamma than of IFN-alpha or IFN-beta. Moreover, the degree of the enhancing effect increased with increasing concentrations of IFN-gamma but not with increasing concentrations of IFN-alpha or IFN-beta. Enhancing effects as high as 14 fold were observed when cells were treated with 100 units/ml of IFN-gamma and the data further suggested that this enhancing effect was not yet approaching a peak value. The dramatic enhancing effect of elevated temperature was also observed for recombinant DNA-derived IFN-gamma.

These studies have been extended to a malignant epithelial mouse cell line, D-11a. The results using D-11a are in agreement with the observations noted above with respect to B-16 melanoma cells, demonstrating that such observations are general in nature. These results further indicate that a combination treatment regimen of specifically induced hyperthermia and interferon therapy, particularly IFN-gamma therapy, may provide a highly potent antitumor effect.

In addition, studies on the combined effects of the combination interferon treatment discussed in Section A above and hyperthermia indicate an antiproliferative effect which promises to be highly effective. Combinations of interferons (IFN-gamma plus IFN-beta) gave a three to six fold enhancement at 37° C. due solely to the synergistic interactions of the interferons. However, incubation of the treated cells at the elevated temperature further enhanced the antiproliferative effect of the combination of interferons to give total enhancements of up to 40-fold (see Table 1). Moreover, as seen for IFN-gamma alone, the enhancing effects of temperature appeared to increase with increasing concentrations of IFN-gamma plus IFN-beta. The present inventors are confident that in vivo studies will confirm the potency of combination therapy with IFN-gamma and elevated temperature (hyperthermia) against human tumors.

C. Methods of Study

1. Background Methods a. Interferons (1). Murine Interferons

Mouse L cells are used in the production of IFN-alpha/beta. Monolayers are challenged with Newcastle disease virus as described in Fleischmann, et al. (1973), *J. Gen. Virol.*, 20:127-137, incorporated herein by reference. The unpurified IFN-alpha/beta has a specific activity of approximately $10^{4.5}$ units/mg of protein Partially purified IFN-alpha ($10^6$ units/mg of protein) and IFN-beta ($10^7$ units/mg of protein) may be purchased from Lee Biomollecular Research Laboratories.

IFN-gamma is prepared in mouse spleen cell cultures after stimulation of the cells with staphylococcal enterotoxin A (SEA) by the method of Osborne, et al. (1979), *Infect. Immun.*, 23:80-86, incorporated herein by reference. The unpurified IFN-gamma preparations are harvested after three days of mitogen stimulation and generally have a specific activity of about $10^{1.7}$ units/mg of protein. Partially purified IFN-gamma ($10^4$ units/mg of protein) is prepared by sequential chromatography on controlled pore glass in 1M Tetra ethyl ammonium chloride and 1M NaCl in phosphate buffered saline (PBS elution) and Ultrogel AcA 54 (1 M NaCl in PBS elution) columns. Recombinant DNA-derived IFN-gamma may be obtained from the American Cancer Society. As yet, there are no commercial sources of murine IFN-gamma known to the inventor.

(2). Human Interferons

IFN-alpha, IFN-beta and IFN-gamma may be purchased from various commercial sources (e.g., Lee Biomolecular Research Laboratories; Ventrex Laboratories; Interferon Sciences, Inc.; Triton Biosciences Inc.; HEM Research Incorporated; AM Gen Biologicals). Recombinant DNA-derived IFN-alpha has been obtained through an agreement with Dr. Sidney Pestka at the Roche Institute and recombinant DNA-derived IFN-gamma has been obtained through an agreement with Dr. Walter Fiers, University of Ghent. However, IFN-gamma may be prepared by the method of H.M. Johnson, F. Dianzani, J.A. Georgiades, "Large scale induction and production of human and mouse interferons." In: *Methods of Enzyology*, Vol. 78A (S. Pestka, ed.) 1981: pp 158-162, incorporated herein by reference.

b. Interferon Titration by Plaque Reduction

B-16 melanoma cells were plated as confluent monolayers on 35-mm plastic Petri dishes (Lux) at a concentration of $10^{6.08}$ cells/dish and were split into two groups which were incubated at either 37.3 or 39.4° for 6-8 h in growth medium as described above. The monolayers were overlaid in triplicate, with fresh growth medium or with serial dilutions of the various interferons in fresh growth medium and were returned to incubate at the appropriate temperature for 14-16 h. The monolayers were then challenged with Mengo virus (Franklin isolate) at a multiplicity of infection of 100 plaque forming units/Petri dish. Mengo virus was used because, unlike vesicular stomatitis virus, its plating efficiency was identical at 37.3 and 39.4° C. After a 45-min incubation for virus absorption, the monolayers were overlaid with a starch overlay, as described in Fleischmann, et al. (1973), *J. Gen. Virol.*, 20:127-137 (incorporated herein by reference). Plaques were developed after 18-20 h and were visualized by decanting the starch overlay and staining the monolayers with 1% crystal violet in 20% methanol (w/v), as described in Fleischmann (1982), *Cancer Res.*, 42:869-875, incorporated herein by reference. Interferon titers were determined by the Karber estimate (Karber, et al. (1981), *Arch. Exp. Pathol. Pharmakol.*, 162:480-487), were calibrated on the WHO international reference preparation G002-904-511 (NIH), and were expressed as the reciprocal of the dilution of interferon which reduced plaque counts to 50% of the control levels.

c. Single Cycle Virus Growth Experiments

B-16 melanoma cells were plated as confluent monolayers in 96-well microtiter plates (Falcon) at a concentration of $10^{4.75}$ cells/well and were split into two groups which were incubated at either 37.3 or 39.4° C. for 6-8 h in growth medium containing 10% fetal calf serum, as described above. The monolayers were overlaid with fresh growth medium or with serial dilutions of the various interferons in fresh growth medium and were returned to incubate at the appropriate temperature for 14-16 h. The monolayers were challenged with Mengo virus at a multiplicity of infection of 10 plaque forming units/cell in a single cycle virus growth experiment. After a 45-min incubation for virus absorption, the monolayers were washed three times to remove unabsorbed parental virus, overlaid with 0.1 ml of fresh growth medium, and returned to incubate at the appropriate temperature. Progeny viruses were harvested 24 h postinfection and stored at −20° C. until titrated by plaque assay, as described by Fleischmann (*J. Gen. Virol.*).

d. Antiproliferative Experiments

The antiproliferative effects of interferons and elevated temperature were studied using cloning experiments. Log phase B-16 melanoma cells were passaged and incubated at 37.3° C. 18-24 h prior to their use in cloning experiments, as described by Fleischmann (*Cancer Res.*). The B-16 melanoma cells were plated at 300 cells/35-mm Petri dish into growth medium or with serial dilutions of the various interferons in growth medium. The plated cells were divided into two sets for 6 days of incubation either at 37.3° C. or at the elevated temperatures. The plates were stained with crystal violet and the number of clones were counted. Clones were defined as 2 or more cells of identical morphology in close proximity. This definition of clone size was chosen because the definition of a clone on the basis of a single replication event provided the most definitive and rigorous evaluation of the antiproliferative effectiveness of interferon possible. Experiments were performed in triplicate or quadruplicate. Control plates incubated at 37.3° C. had a cloning efficiency of about 60%. Control plates incubated at 39.4° C. had a cloning efficiency of about 45%. The data were expressed either as the percentage of the control number of clones or as fold inhibition (the reciprocal of the percentage of the control number of clones).

Determinations of additivity or synergism were obtained in the method of Spector, et al. (1982), *Am. J. Med.*, 73:36–39, incorporated herein by reference, where the combination index (C.I.)=1n (number of clones with hyperthermia treatment)+1n (number of clones with interferon treatment)−1n (number of clones with no treatment)−1n (number of clones with combined hyperthermia and interferon treatment). Additive: $0+2$ SE$>$C.I.$>0-2$ SE; synergistic: C.I.$>0+2$ SE; antagonistic: C.I.$<0-2$ SE.

EXAMPLE 1

Differential Enhancement of IFN-gamma Antiproliferative Activity at Elevated Temperatures To accurately evaluate the effect of elevated temperatures on the antiproliferative activities of the three interferons, replicate cloning cultures of B-16 melanoma cells were plated simultaneously at four different incubation temperatures and with IFN-alpha, IFN-beta or IFN-gamma. The antiproliferative activity of the interferons was observable as a reduction in the relative cloning efficiency of the B-16 melanoma cells. FIG. 1 presents the averaged results of three experiments. Incubation at elevated temperatures had a slight effect on the cloning efficiency of untreated B-16 melanoma cells. For example their cloning efficiency at 39.4° C. was reduced to about 75% of their cloning efficiency at 37.3° C. To account for these slight effects of elevated temperatures, the data of FIG. 1 and all subsequent charts are plotted as the percentage of the control value at each incubation temperature. As seen in FIG. 1, the antiproliferative activities of IFN-alpha and IFN-gamma were enhanced approximately equally by increasing temperatures. This is indicated by their similar slopes ($-0.22$ for IFN-alpha and $-0.25$ for IFN-beta). The enhancing effect of increasing temperatures on IFN-gamma antiproliferative activity appeared to be more dramatic, as indicated by the much steeper slopes for IFN-gamma ($-0.48$).

The degree of enhancement which occurred at the elevated temperatures was estimated by comparing the fold inhibition of clone development at 39.4° C. with that observed at 37.3° C. Fold inhibition of clone development was expressed as the reciprocal of the percentage of control cloning efficiency. Table 1 presents the data from FIG. 1 evaluated in this manner. It can be seen that, for each interferon and for each temperature, the two treatments provided a synergistic effect. Further, there was an increasing enhancement of antiproliferative activity of each interferon with increasing temperature. At 39.4° C. there was an approximately 3-fold level of enhancement of IFN-alpha and IFN-beta. In contrast there was an approximately 10-fold level of enhancement of IFN-gamma antiproliferative activity at 39.4° C. (range for 3 experiments was 6.5- to 17-fold). Thus the degree of enhancement by elevated temperatures varied among the interferons, with the antiproliferative activity of IFN-gamma being most strong enhanced.

TABLE 1

Enhancement of Antiproliferative Activities of Interferons by Elevated Temperatures

| Interferon | Temperature (°C.) | % of control clones | Fold inhibition[a] | Ratios relative to 37.3° C. |
|---|---|---|---|---|
| MuIFN-alpha | 37.3° | 44 | 2.3 | |
| (3000 units/ml) | 38.1 | 34 | 2.9 | 1.3 (syn)[b] |
| | 38.6 | 29 | 3.4 | 1.5 (syn) |
| | 39.4 | 15 | 6.7 | 2.9 (syn) |
| MuIFN-beta | 37.3 | 37 | 2.7 | |
| (3000 units/ml) | 38.1 | 27 | 3.7 | 1.4 (syn) |
| | 38.6 | 21 | 4.8 | 1.8 (syn) |
| | 39.4 | 11 | 9.1 | 3.4 (syn) |
| MuIFN-gamma | 37.3 | 31 | 3.2 | |
| (30 units/ml) | 38.1 | 15 | 6.2 | 2.1 (syn) |
| | 38.6 | 9.4 | 11 | 3.4 (syn) |
| | 39.4 | 3.0 | 33 | 10 (syn) |

[a] Reciprocal of percentage of control clones.
[b] Syn, synergistic interaction of elevated temperature and interferon, determined according to the method of Spector, et al.

EXAMPLE 2

Effect of Elevated Temperature on the Antiproliferative Activity of Natural and Recombinant DNA-derived IFN-gamma To ascertain whether the enhanced antiproliferative activity of IFN-gamma seen with elevated temperatures was due to IFN-gamma itself, the antiproliferative activities of a crude preparation of natural IFN-gamma and a highly purified recombinant DNA-derived IFN-gamma preparation were compared. The results of a representative experiment are shown in Table 2. Again for each interferon, the elevated temperature synergistically enhanced the antiproliferative activity. In this experiment IFN-alpha antiproliferative activity was enhanced 2.5-fold by incubation at the elevated temperature. Both the crude preparation of natural IFN-gamma and the highly purified recombinant DNA-derived IFN-gamma preparation had their antiproliferative activities enhanced 8.3-fold by incubation at the elevated temperature. Thus it was most likely the IFN-gamma itself rather than contaminating lymphokine which was responsible for the enhanced antiproliferative activity at the elevated temperature.

TABLE 2

Effect of Elevated Temperature on the Antiproliferative Activity of Natural and Recombinant DNA-Derived MuIFN-gamma

| Interferon | Temperature (°C.) | % of control clones | Fold inhibition[a] | Ratios relative to 37.3° C. |
|---|---|---|---|---|
| MuIFN-alpha | 37.3° | 46 | 2.2 | |
| (3000 units/ml) | 39.4 | 18 | 5.6 | 2.5 (syn)[a] |
| MuIFN-gamma | 37.3 | 42 | 2.4 | |
| (30 units/ml) | 39.4 | 5.0 | 20 | 8.3 |
| MuIFN-gamma | 37.3 | 41 | 2.4 | |
| (30 units/ml) | 39.4 | 5.0 | 20 | 8.3 |

[a] Syn, synergistic interaction of elevated temperature and interferon, determined according to the method of Spector, et al.; MuIFN-gamma, naturally produce MuIFN-gamma; MuIFN-gama, MuIFN-gamma produced by recombinant DNA techniques.

EXAMPLE 3

Figure 2:
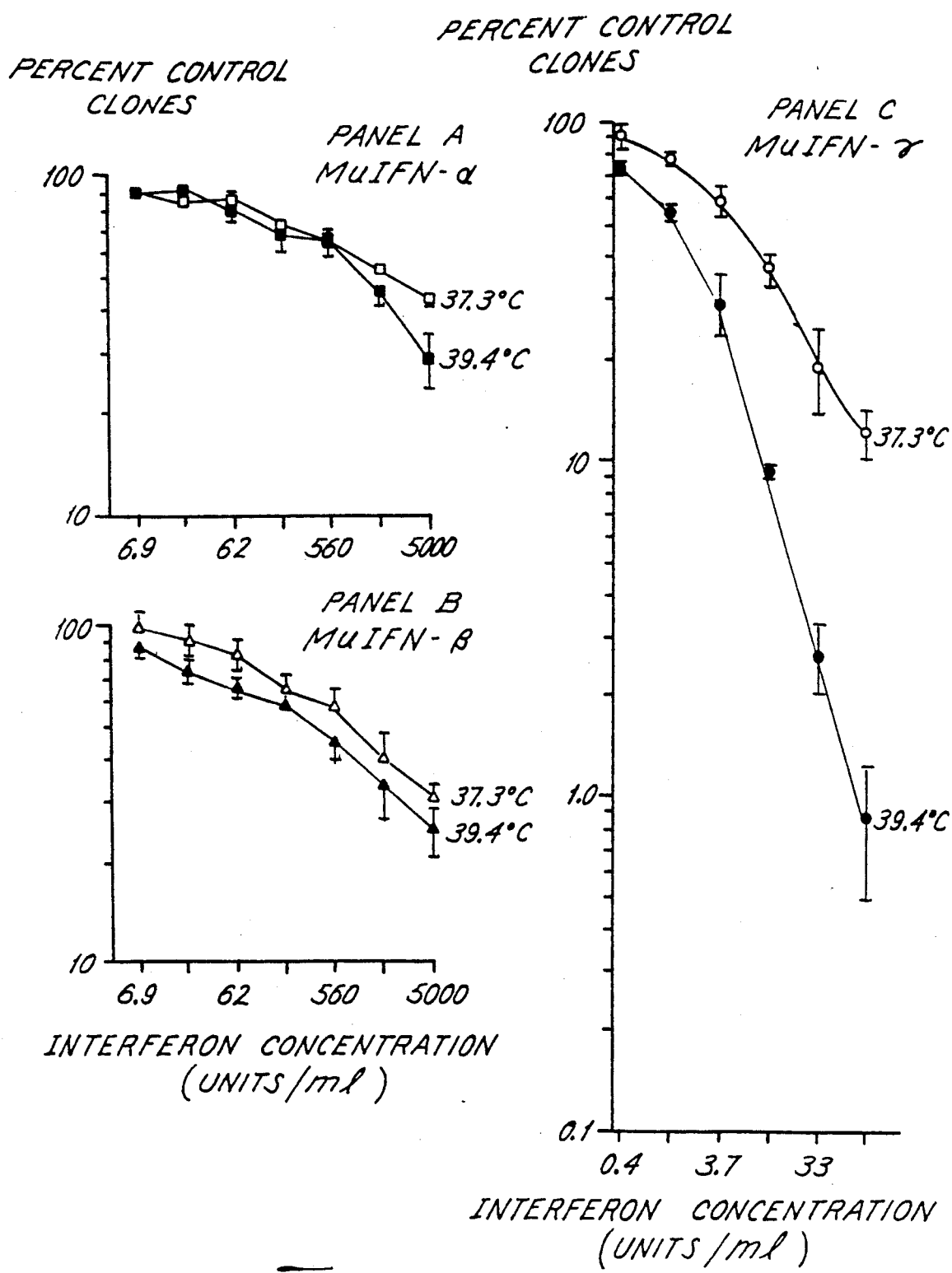
FIG. 2. Effect of interferon concentration on the enhancement of interferon antiproliferative activity at elevated temperature. Log phase mouse B-16 melanoma cells were plated at 300 cells/35-mm Petri dish into growth medium or serial dilutions of IFN-alpha (■, □), IFN-beta (▲, △), or IFN-gamma (●, ○). Replicate sets of plates were incubated for 6 days at 37.3° C. (□, △, ○) or 39.4° C. (■, ▲, ●) in Napco Model 5300 incubators. Experiments were performed in triplicate or quadruplicate. A, IFN-alpha; B, IFN-beta; C, IFN-gamma. Points, mean; bars, SE.

Enhancing the Effect of Heat Increases with Increasing Concentrations of IFN-gamma The effect of elevated temperature on the antiproliferative activities of the three murine interferons was examined for a range of interferon concentrations. B-16 melanoma cloning studies were performed at 37.3 and 39.4° C. FIG. 2 presents the averaged results of three experiments. As shown in FIG. 2, A and B, incubation of B-16 melanoma cells at the elevated temperature caused only a slight enhancement of the antiproliferative activities of IFN-alpha and IFN-beta. As shown in FIG. 2C, IFN-gamma had a much more potent antiproliferative effect against B-16 melanoma cells than did either IFN-alpha or IFN-beta. Moreover the antiproliferative effect of IFN-gamma was dramatically enhanced by elevated temperatures across a range of IFN-gamma concentrations. Similar results were obtained with highly purified recombinant DNA-derived IFN-gamma.

The degree of enhancement which occurred at the elevated temperature is presented in Table 3. Only relatively low levels of enhancement by elevated temperature were observed across the whole range of IFN-alpha and IFN-beta concentrations, and a synergistic enhancement was observed only for the highest interferon concentrations tested. However, for IFN-gamma, the enhancing effect of elevated temperature increased with increasing IFN-gamma concentrations, showing a synergistic enhancement at all but the lowest interferon concentration tested, and reached a 14-fold enhancement for 100 units/ml. This value approximates the maximal effect of elevated temperature which can be demonstrated using this technique (because the clone number is approaching zero), but may not represent the maximal effect which can occur.

The enhanced ability of IFN-gamma to synergistically interact with elevated temperature was not due to the greater relative potency of IFN-gamma. Concentrations of IFN-gamma which reduced the number of clones at 37° C. to 79 and 59% of the control were synergistically enhanced at the elevated temperature, while those concentrations of IFN-alpha and IFN-beta which reduced the number of clones at 37° C. to those same levels were not synergistically enhanced at the elevated temperature. These data suggest a basic difference in the effect of elevated temperature on IFN-gamma as compared to IFN-alpha and IFN-beta.

Figure 3:
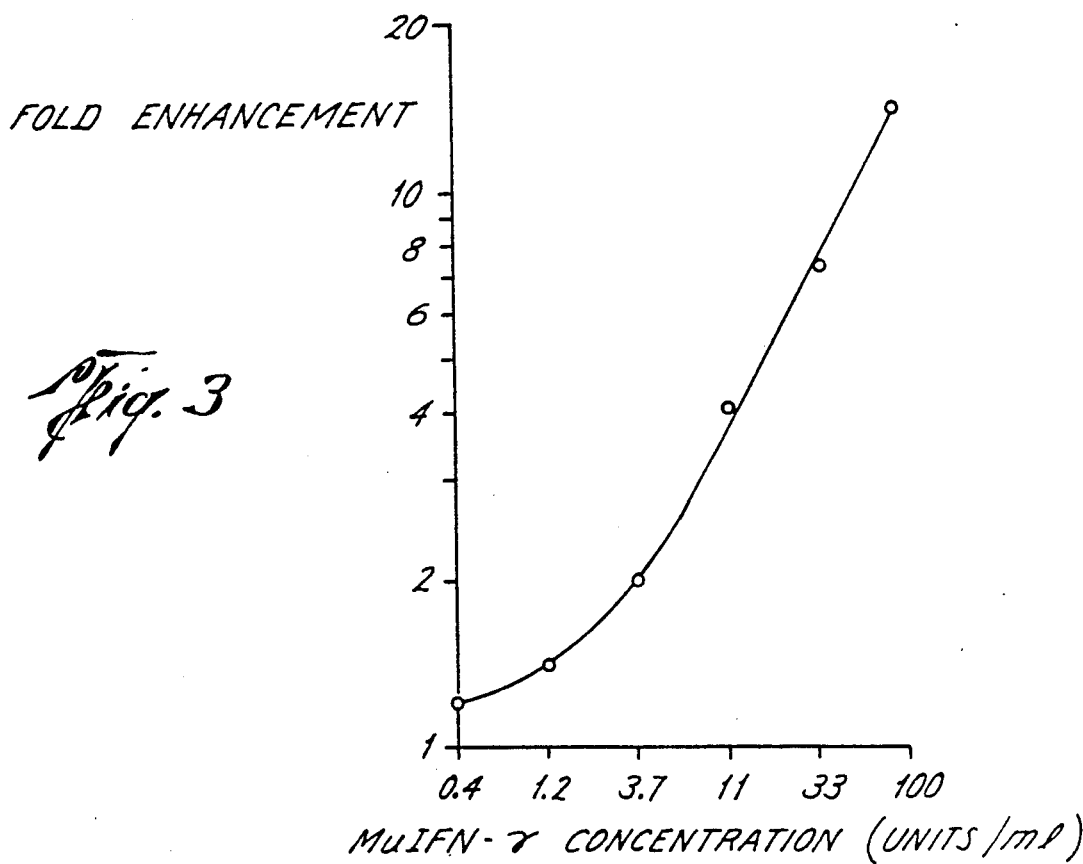
FIG. 3. Enhancing effect of elevated temperature increases with IFN-gamma concentration.

FIG. 3 plots the fold enhancement at 39.4° C. for increasing concentrations of IFN-gamma. The relative enhancing effect of elevated temperature can be seen to increase progressively with increasing concentrations of IFN-gamma. The data suggest that the maximal level of enhancement may not yet have been obtained and might continue to increase as the IFN-gamma concentration increases.

TABLE 3

Effect of Interferon Concentrations on Enhancement of Antiproliferative Activities of Interferons by Elevated Temperature

| Interferon Type | Units/ml | 37.3° C. % of control clones | 37.3° C. Fold inhibition | 39.4° C. % of control clones | 39.4° C. Fold inhibiton | Ratio 39.4° C./37.3° C. |
|---|---|---|---|---|---|---|
| MuIFN-alpha | 6.9 | 92 | 1.1 | 92 | 1.1 | 1.0 (add)[a] |
| | 21 | 86 | 1.2 | 93 | 1.1 | 0.9 (add) |
| | 62 | 87 | 1.1 | 81 | 1.2 | 1.1 (add) |
| | 190 | 73 | 1.4 | 69 | 1.4 | 1.0 (add) |
| | 560 | 65 | 1.5 | 67 | 1.5 | 1.0 (add) |
| | 1700 | 53 | 1.9 | 46 | 2.2 | 1.2 (add) |
| | 5000 | 43 | 2.3 | 29 | 3.4 | 1.5 (syn) |
| MuIFN-beta | 6.9 | 100 | 1.0 | 88 | 1.1 | 1.1 (add) |
| | 21 | 92 | 1.1 | 75 | 1.3 | 1.2 (add) |
| | 62 | 83 | 1.2 | 67 | 1.5 | 1.3 (add) |
| | 190 | 66 | 1.5 | 60 | 1.7 | 1.1 (add) |
| | 560 | 58 | 1.7 | 46 | 2.2 | 1.3 (add) |
| | 1700 | 40 | 2.5 | 34 | 2.9 | 1.2 (add) |
| | 5000 | 31 | 3.2 | 25 | 4.0 | 1.3 (syn) |
| MuIFN-gamma | 0.4 | 91 | 1.1 | 75 | 1.3 | 1.2 (add) |
| | 1.2 | 79 | 1.3 | 55 | 1.8 | 1.4 (syn) |
| | 3.7 | 59 | 1.7 | 29 | 3.4 | 2.0 (syn) |
| | 11 | 37 | 2.7 | 9.3 | 11 | 4.1 (syn) |
| | 33 | 19 | 5.3 | 2.6 | 38 | 7.2 (syn) |
| | 100 | 12 | 8.3 | 0.87 | 115 | 14 (syn) |

[a]Add, additive interaction of elevated temperature and interferon; syn, synergistic interaction of elevated temperature and interferon, both determined according to the method of Spector, et al.

EXAMPLE 4

Effect of Elevated Temperature on Antiviral Activity of Interferon

Figure 4:
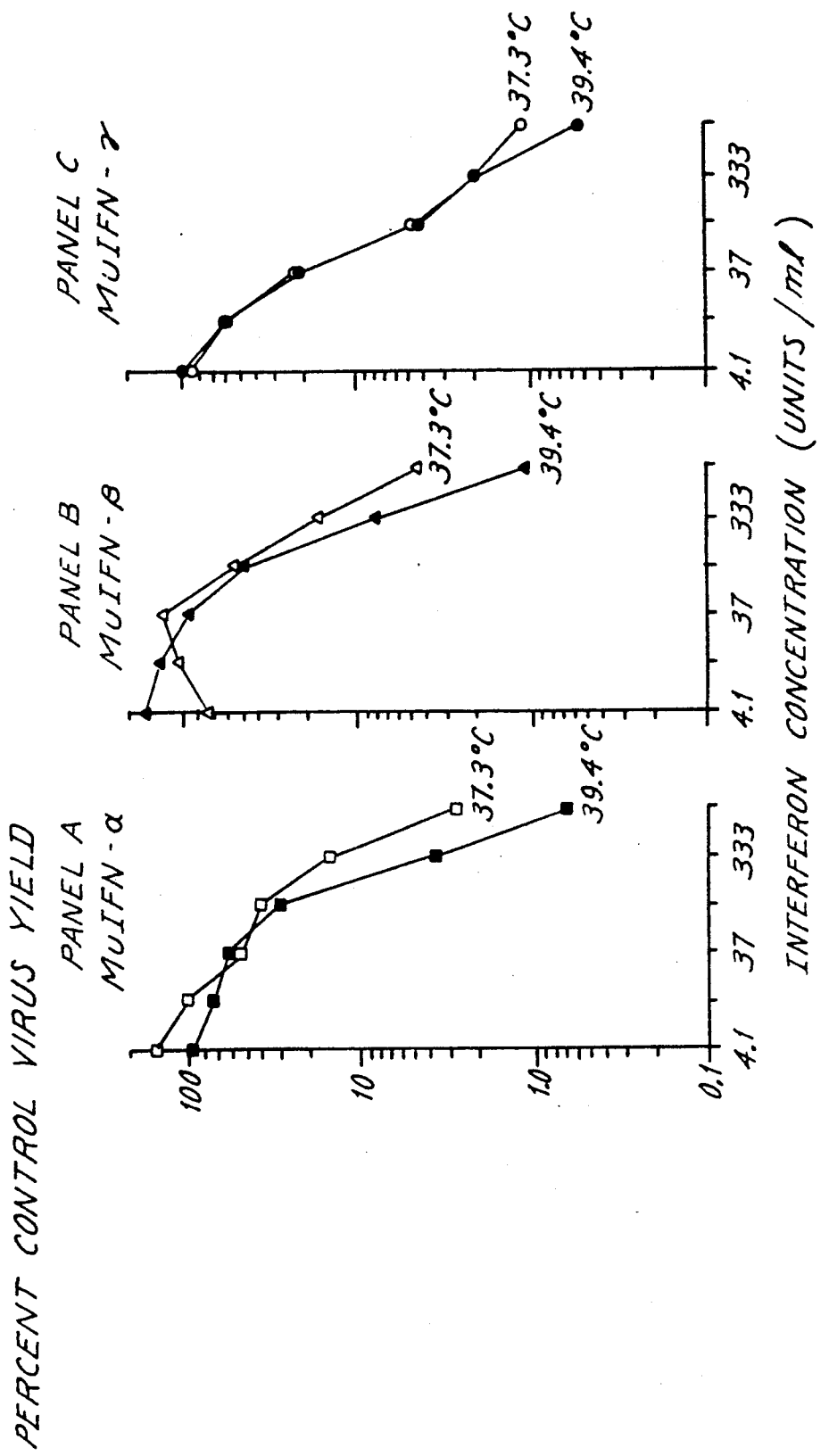
FIG. 4. Effect of elevated temperatures on the antiviral activities of interferons. Confluent monolayers of mouse B-16 melanoma cells were treated with growth medium or serial dilutions of IFN-alpha (□, ■), IFN-beta (△, ▲), or IFN-gamma (○, ●). Replicate sets of plates were incubated for 14-16 h either at 37.3° C. (□, △, ○) or at 39.4° C. (■, ▲, ●) in Napco Model 5300 incubators. Next the monolayers were challenged with Mengo virus at a multiplicity of infection of 10 plaque forming units/cell. After a 45-min incubation period the unabsorbed parental virus was removed by a triple wash and the monolayers were overlaid with fresh media and reincubated at the appropriate temperature. Progeny viruses were harvested 24 h postinfection and stored at $-20°$ C. until titrated by plaque assay. A, IFN-alpha; B, IFN-beta; C, IFN-gamma.

In order to determine whether the differentially enhanced antiproliferative potency of IFN-gamma at 39.4° C. was a part of a general enhancement of IFN-gamma activities, the effect of elevated temperature on IFN-gamma antiviral activity was examined. B-16 melanoma cells were treated with IFN-alpha, IFN-beta, and IFN-gamma at 37.3 and 39.4° C. and were used for single cycle virus growth experiments. Following interferon pretreatment the cells were challenged with Mengo virus and were incubated at 37.3 or 39.4° C. until progeny virus were harvested at 24-h postinfection. FIG. 4 presents the interferon sensitivity curves for Mengo virus for a representative experiment. Incubation at 39.4° C. had a slight, inhibitory effect on the replication of Mengo virus. The yield of progeny viruses by untreated B-16 melanoma cells grown at 39.4° C. was reduced to about 50% of the yield at 37.3° C.

Thus the data of FIG. 4 are plotted as the percentage of the control virus yield at the appropriate temperature.

As shown in FIG. 4, A and B, the antiviral activities of IFN-alpha and IFN-beta were enhanced by 2- to 3-fold when the experiment was performed at 39.4° C. These results paralleled those observed for the antiproliferative activity of IFN-alpha and IFN-beta. However, the interferon sensitivity curves of IFN-gamma generated at 37.3 and 39.4° C. were virtually identical (FIG. 4C). These results indicated that, in contrast to the observations on the enhancement of the antiproliferative activity of IFN-gamma, the elevated temperature had little or no effect on the antiviral activity of IFN-gamma.

EXAMPLE 5

Synergistic Enhancement of Combination Interferon Treatment by Hyperthermia

Experimental data had indicated that potentiation of interferon's antiproliferative activity by combination interferon treatment occurred at both 39.4° C. and at 37.3° C. The question remained whether the potentiation levels observed with combination interferon treatment were enhanced at the elevated temperature. In Table 4, the numbers of clones obtained at 37.3° C. and at 39.4° C. were compared for each of the combinations of the two interferons. This presentation of the data allows the direct evaluation of the effect of hyperthermia according to the method of Spector, et al. Hyperthermic conditions reduced the number of clones on control plates by 1.3-fold. It can be seen that, at the highest interferon concentrations used, the level of enhancement was indeterminant. However, slightly lower concentrations of interferons were enhanced by 20- to 34-fold. Even the lowest concentrations of interferons used were enhanced by 3-fold. Thus, the amount of enhancement was dependent on the concentrations of each of the two interferons. Further evaluation of the data by the method of Spector, et al. shows that the hyperthermic conditions did synergistically enhance the already potent antiproliferative activities obtained with combination interferon treatment.

TABLE 4

| IFN-gamma concentration (units/ml) | Parameter | Synergistic Enhancement of Combination Interferon Treatment by Hyperthermia ||| 
| | | IFN-alpha/beta concentration |||
| | | 28 units/ml | 83 units/ml | 250 units/ml |
| --- | --- | --- | --- | --- |
| 0.31 | No. of clones at 37.3° C. | 112.0 | 79.7 | 51.7 |
| | No. of clones at 39.4° C. | 36.7 | 24.7 | 9.7 |
| | Fold enhancement | 3.1 (Syn)[a] | 3.2 (Syn) | 5.3 (Syn) |
| 0.93 | No. of clones at 37.3° C. | 77.0 | 53.3 | 37.7 |
| | No. of clones at 39.4° C. | 18.7 | 9.7 | 2.0 |
| | Fold enhancement | 4.1 (Syn) | 5.5 (Syn) | 19 (Syn) |
| 2.8 | No. of clones at 37.3° C. | 50.7 | 40.7 | 20.7 |
| | No. of clones at 39.4° C. | 4.7 | 2.0 | 1.0 |
| | Fold enhancement | 11 (Syn) | 20 (Syn) | 21 (Syn) |
| 8.3 | No. of clones at 37.3° C. | 26.0 | 11.3 | 4.0 |
| | No. of clones at 39.4° C. | 2.0 | 0.33 | 0.0 |
| | Fold enhancement | 13 (Syn) | 34 (Syn) | IND |

[a]Syn, synergistic interaction of elevated temperature and interferon, determined according to the method of Spector, et al.; IND, indeterminant.

It should be noted that the data of Table 4 show the synergistic enhancement of an already potentiated antiproliferative activity. To more fully appreciate the total contributory effects of hyperthermic conditions and combination interferon treatment, the level of antiproliferative activity observed for combination interferon treatment at 39.4° C. should be compared with the level of antiproliferative activity expected on the basis of the activities of the individual interferons at 37.3° C. When compared in this manner, the level of enhancement of the antiproliferative effect of interferon can be seen to increase as the concentration of each of the two types of interferons increases. Further, at the higher interferon concentrations used, the total effect of hyperthermia and combination interferon treatment was very dramatic, reaching levels as high as 50-fold to 150-fold for modest interferon concentrations (250 units of IFN-alpha/beta per ml plus 2.8 units of IFN-gamma per ml and 83 units of IFN-alpha/beta per ml plus 8.3 units of IFN-gamma per ml, respectively). At higher interferon concentrations, the total effect was indeterminant, because the number of clones developing with hyperthermia and combination interferon treatment was reduced to zero.

EXAMPLE 6

Hyperthermia Enhancement of Human IFN-gamma

Experiments were carried out in a fashion identical to the foregoing, except that human IFN's were tested for hyperthermic-enhancement using human tumor target cells. In particular, human IFN preparations of IFN-alpha, beta and gamma were tested against G-361 and WISH cells in a similar fashion as described above for the murine system. Virtually identical results were obtained At IFN-alpha concentrations of 5000 units/ml, approximately 44% of control clones remained after treatment at 37° C. whereas only approximately 29% of control clone remained after treatment at the elevated temperature of 39.5° C. Although little enhancement was noted for IFN-beta at the elevated temperature, treatment with IFN-gamma at the elevated temperature demonstrated a profound enhancement. At an IFN-gamma concentration of 1000 units/ml, only 13% of control G-361 clones remained following the 39.5° C. treatment as compared to a 50% reduction at 37° C. This works out to an approximate 4-fold enhancement for IFN-gamma at a concentration of 1000 units/ml.

A similar result was obtained with WISH cells. At 1000 units/ml, IFN-gamma demonstrated a 97.6% reduction in control clones cells at the elevated temperature as compared to an 88% reduction at 37° C. This works out to an overall enhancement of 5-fold for IFN-gamma treatment at 39.5° C.

The foregoing examples indicate that an enhancement of the antiproliferative activity of IFN-gamma by elevated temperature was more dramatic than that seen for either IFN-alpha or IFN-beta and represented a highly potent synergism. The enhancement of the antiproliferative activity of 30 units of IFN-gamma increased with increasing temperature, reaching a 6.5- to 17-fold enhancement at 39.4° C. This differential enhancing effect of elevated temperature was not simply a consequence of the greater relative potency of IFN-gamma against B-16 melanoma cells treated at 37.3° C. At concentrations producing the same level of antiproliferative effect at 37.3° C., the three interferons demonstrated a differential enhancement of antiproliferative activity at 39.4° C. In addition the greater relative antiproliferative activity of IFN-gamma at elevated temperatures was not the results of a greater perception of IFN-gamma titer at the elevated temperature, since the three murine interferons had approximately the same relative antiviral titers at 37.3 and 39.4° C. Further, the greater relative antiproliferative activity of IFN-gamma at elevated temperatures was not the result of a greater stability of IFN-gamma to the elevated temperature, since the three murine interferons had approximately equal relative stabilities at the elevated temperature. Finally, results obtained using highly purified, recombinant DNA-derived IFN-gamma indicated that it was most probably IFN-gamma itself and not another lymphokine which was responsible for the enhanced antiproliferative effect at the elevated temperatures. Thus these data indicate that the potency of IFN-gamma was enhanced by elevated temperatures and that the degree of enhancement was greater for IFN-gamma than for IFN-gamma or IFN-beta.

Perhaps more importantly, unlike IFN-alpha and IFN-beta, the degree of enhancement of IFN-gamma antiproliferative activity by elevated temperature and the potency of the synergistic interaction increased with increasing concentrations of IFN-gamma. Across a range of interferon concentrations, IFN-alpha and IFN-beta antiproliferative activities were the same or only slightly (2- to 3-fold) enhanced at the elevated temperature, and demonstrated synergism only at the highest interferon concentrations used. However, for IFN-gamma, the level of enhancement and, therefore, the degree of synergism by elevated temperature was dependent on the concentration of IFN-gamma and increased with increasing IFN-gamma concentration. A 14-fold level of enhancement was seen with 100 units of IFN-gamma/ml. The data suggest that the maximal level of enhancement may not have been obtained and that the level of enhancement might continue to increase with increasing IFN-gamma concentration. Thus the differential enhancement of the antiproliferative activity of IFN-gamma occurs across a range of IFN-gamma concentrations and increases with increasing IFN-gamma concentration.

The above data evaluated the enhancement by hyperthermia of the antiproliferative activity of combined interferon treatments. However, it did not take into account the enhancement which had already occurred by combining the interferons (potentiation). When this was considered, the total combined antiproliferative effect of hyperthermia and combination interferon treatment was seen to be very potent. Total enhancement levels as high as 50-fold and 150-fold were observed. Again, the data suggest that these did not represent maximal obtainable values but more likely represented maximal demonstrable values because of the high potency of the treatment and of the limitations of the technique (total elimination of clone development).

Thus, the foregoing examples indicate the usefulness of eliciting an enhanced IFN-gamma efficacy in patients through the imposition of an artificial temperature elevation in such patients. For systemic IFN-gamma therapy, this can be achieved most readily, for example, through the use of a temperature-controlled blanket or through the application of ultrasound therapy. Where the IFN-gamma is administered s.c. or i.m., heat should preferably be applied following administration. Artificial temperature elevation is a technique commonly employed in other clinical settings, for example, it is used as a single agent in the treatment of neoplastic disease (Robins, H.I. Role of whole-body hyperthermia in the treatment of neoplastic disease and hypertension in mice. Cancer Res 44: (Suppl.) 4878-4883s, 1984), and is therefore well within the skill of the art. Following IFN administration, one would want to elevate the patient's body temperature in a controlled manner to between approximately 37.3° C. and about 40.5° C., preferably about 39.4° C. After a satisfactory body temperature has been achieved, the IFN-gamma preparation should be administered in amounts generally found to be non-toxic and efficacious. Typically, dosage ranges between about $1 \times 10^6$ and $50 \times 10^6$ units/dose are employed. The patient's body temperature may be maintained at this level in a constant fashion or, more preferably, heat is applied approximately 4-6 hours post IFN administration, when the IFN level in blood has reached a substantial level. The patient's body temperature may then be allowed to return to normal after approximately 2 to 4 hours, as tolerated by the patient. This time period will allow sufficient time for the temperature enhancement to be effective, yet relieving the patient from potential discomfort associated with hyperthermia.

D. Treatment Protocols to Inhibit the Development of Interferon-Associated Resistance A significant problem associated with the prolonged use of IFN-alpha and/or IFN-beta in interferon therapy is the rapid development of resistance, which results in a profound apparent loss of sensitivity of target cells to such therapy. However, it has been determined that through carefully structured treatment protocols, such resistance may be effectively reduced or avoided altogether.

The clinical development of IFN-associated resistance is closely paralleled by the development of resistance in cells cultured in vitro in the presence of either IFN-alpha or IFN-beta, alone or in combination. Studies which form the basis of this observation have evaluated the in vitro kinetics of the antiproliferative activities of the three different murine interferons using a cloning technique. B-16 melanoma cells developed a resistance to the antiproliferative effects of IFN-alpha and IFN-beta with more than 2 to 4 days of treatment. This quickly developing resistance was relatively stable as the cells only gradually recovered their sensitivity over a period of several weeks. Moreover, the results were not an artifact of interferon disappearance or decay, since readdition of the interferons at daily intervals did not alter the response. The results were not reflective of a total resistance to interferon's antiproliferative activity, since the cells retained their sensitivity to IFN-gamma. These results suggested that tumor cells constantly treated with IFN-alpha and IFN-beta rapidly developed resistance to the antiproliferative activities of these interferons.

B-16 cells treated with IFN-gamma retained their sensitivity to the antiproliferative activity of the interferon. Further, IFN-gamma treatment could both block the development of resistance to IFN-alpha and IFN-beta and restore a resistant population to sensitivity to IFN-alpha and IFN-beta. Finally, cells grown in IFN-alpha and IFN-beta (and therefore resistant to IFN-alpha and IFN-beta) responded to IFN-gamma treatment in a potentiated manner, suggesting that part of the antiproliferative activity of IFN-alpha and IFN-beta was present even though it was not directly manifested.

Current IFN-alpha clinical protocols involve the daily or thrice weekly injection of the interferon. However, it appears as though such protocols might select resistant cells and thus may not provide the maximal possible antitumor effect. The present studies further indicate that alternate or combination treatment with IFN-gamma might be routinely employed to maintain the sensitivity of the tumor cells to IFN-alpha.

In addition, studies which evaluated the kinetics of development and maintenance of the antiviral state suggested that for mengovirus and vaccinia, the IFN-alpha and IFN-beta induced antiviral state decayed rapidly upon removal of the interferon. The decay of the antiviral state was found to be dependent on de novo synthesis of RNA and protein, suggesting that it represented a natural control mechanism. The antiviral state induced by IFN-gamma increased for the first 12 hours following removal of the interferon and then slowly decayed. It has been shown that combination treatment with IFN-gamma can prevent the antiviral state decay which occurs, following IFN-alpha or IFN-beta removal. These results suggest that treatment with IFN-gamma or combinations of IFN-gamma with IFN-alpha or IFN-beta may be the treatment of choice for control of viral disease in man.

Taken together, these studies indicate that combination interferon treatment with IFN-gamma and IFN-alpha or IFN-beta may be a highly effective method for controlling cancers and viral diseases in man. Indeed, a number of clinical trials evaluating the efficacy of combination interferon therapy are now underway in the U.S. and abroad. However, these studies may be premature. It is still necessary to identify the best treatment schedule, the most effective dosages of the interferons, and the best administration routes for the interferons. These treatment studies are an important focus of the present disclosure.

A cloning system using mouse B-16 melanoma cells and human G-361 melanoma cells was employed to explore the kinetics of development of the antiproliferative activities of IFN-alpha, IFN-beta and IFN-gamma. Cells were cloned in interferon which was removed at varying times from the start of the experiment and replaced with growth medium. The data showed that IFN-alpha and IFN-beta exert their maximum antiproliferative activity within two to four days of interferon exposure, thereafter developing a resistance to further treatment with IFN-alpha and IFN-beta. The cells did not develop resistance to IFN-gamma.

Accordingly, it is proposed that maximal interferon activity, with a minimal occurrence of interferon-associated resistance, may be achieved by treating the patient with a composition which includes IFN-alpha or IFN-beta for approximately two to four days, followed by the addition of an interferon-gamma containing preparation for approximately the same period of time. The IFN-gamma containing preparation may be administered alone or in combination with either of the type I interferons. In a preferred embodiment, IFN-gamma is administered alone to reduce the overall cost of treatment to the patient, which, due to the expense associated with IFN therapy, can be an important consideration.

Following the two to four day treatment employing the IFN-gamma-containing preparation, the patient is then treated with IFN-alpha and/or beta, for approximately two to four days, with the protocol being continuously shifted from the type I to type II IFN treatment in this manner throughout the overall period of therapy. While it has been determined that a similar effect can be achieved by simply maintaining the patient with a straight combination treatment, that is, through the utilization of IFN-gamma in combination with IFN-alpha and/or beta throughout the period of therapy, the present finding indicates that a significant cost reduction to the patent can be realized, without a loss of apparent efficacy, by administering these agents sequentially in the foregoing manner. The following experiments exemplify this finding.

EXAMPLE 7

Differential Sensitivity of Melanoma Cells to Prolonged Treatment with Alpha, Beta or Gamma Interferons: Development of Resistance to Alpha and Beta Interferons 1. Materials and Methods a. Cells Mouse B-16 melanoma cells (clone F-1) and human G-361 melanoma cells were used in cell cloning experiments. Mouse B-16 melanoma cells were routinely grown in 100mm plastic culture dishes (LUX, Miles Laboratories, Naperville, Ill.) in a growth medium of Eagle's minimal essential medium (Earle's base, GIBCO, Grand Island, N.Y.) supplemented with 10% fetal calf serum (Flow Laboratories, McLean, Va.) 0.22% sodium bicarbonate, penicillin (100 units/ml, Pfizer, New York, N.Y.), streptomycin (100 ug/ml, Pfizer), and gentamycin (11 ug/ml, Invenex, Chagrin Falls, Ohio). Human G-361 melanoma cells were routinely grown in 100mm plastic culture dishes in a growth medium of McCoy's 5A (GIBCO) supplemented with 10% fetal calf serum, 5% donor horse serum (Flow Laboratories), 2mM L-glutamine (Sigma, St. Louis, Mo.), 21 ug/ml L-serine (Sigma), sodium bicarbonate and antibiotics.

b. Interferons

Partially purified murine IFN-alpha ($10^{6.26}$ units/mg of protein) and IFN-beta ($10^{7.04}$ units/mg of protein) were purchased from Lee Biomolecular (San Diego, Calif.). Recombinant DNA-derived murine IFN-gamma (reported as >95% pure at $10^{6.66}$ units/mg of protein) was provided by Drs. Patrick Gray, Ernst Rinderknecht, and Gene Burton of Genentech (San Francisco, Calif.). Partially purified human IFN-alpha ($10^7$ units/mg of protein) was prepared by Dr. Kari Cantell from human peripheral blood leukocytes. Human IFN-beta ($10^5$ units/mg of protein) was purchased from Lee Biomolecular (San Diego, Calif.). Recombinant DNA-derived human IFN-gamma was obtained from Hoffman-LaRoche (Nutley, N.J.).

Interferon titers were determined by a microtiter plaque reduction assay as described for preceding examples. Interferon titers were calibrated using the NIH reference standards G002-904-5114 (for mouse) and G023-901-527 (for human) and were expressed as international reference units/ml.

c. Cloning Experiments

Sub-confluent monolayers of mouse B-16 melanoma cells and human G-361 melanoma cells in log phase growth were fluid changed 18 to 24 hr prior to their use in cloning experiments. Cells were trypsinized, spun out of trypsin, resuspended in growth medium at a concentration of 300 cells/ml, and plated (1 ml volume) on 35 mm plastic petri dishes (Contur dishes, LUX, Miles Laboratories). Dilutions of the various interferon preparations were made in growth medium and 1 ml of the appropriate dilution was added to the plates. Control plates received 1 ml of growth medium. The cells were thoroughly mixed in the plates and the plates were incubated at 37° C. in a humidified, 4% $CO_2$ environment. At various times after plating, the plates were removed from the incubator. The interferon was gently removed and replaced with fresh growth medium. The plates were reincubated. Eight (B-16 melanoma cells) or nine (G-361 melanoma cells) days after plating, the cells were stained with crystal violet (1% crystal violet in 20% methanol [v/v]). Clones were defined as two or more cells of identical morphology in close proximity. This definition of clone size was chosen because it provided the most definitive and rigorous evaluation of the antiproliferative effectiveness of interferon possible.

d. Yield Reduction Experiments

Mouse B-16 melanoma cells which had been cloned and grown in the presence or absence of IFN-alpha were trypsinized, plated at $10^{4.78}$ cells/well in microtiter plates (Falcon), and incubated at 37° C. for 6–8 hours. The cells were overlaid with growth medium or with various interferon dilutions for 16 hours and challenged with mengovirus (Franklin isolate) at a multiplicity of infection of 10. After 45 minutes incubation for virus absorption, the monolayers were washed twice to remove unabsorbed parental virus and progeny virus were harvested 24 hours post-infection. The virus yields were stored at −20° C. until titrated by plaque assay.

Figure 5:
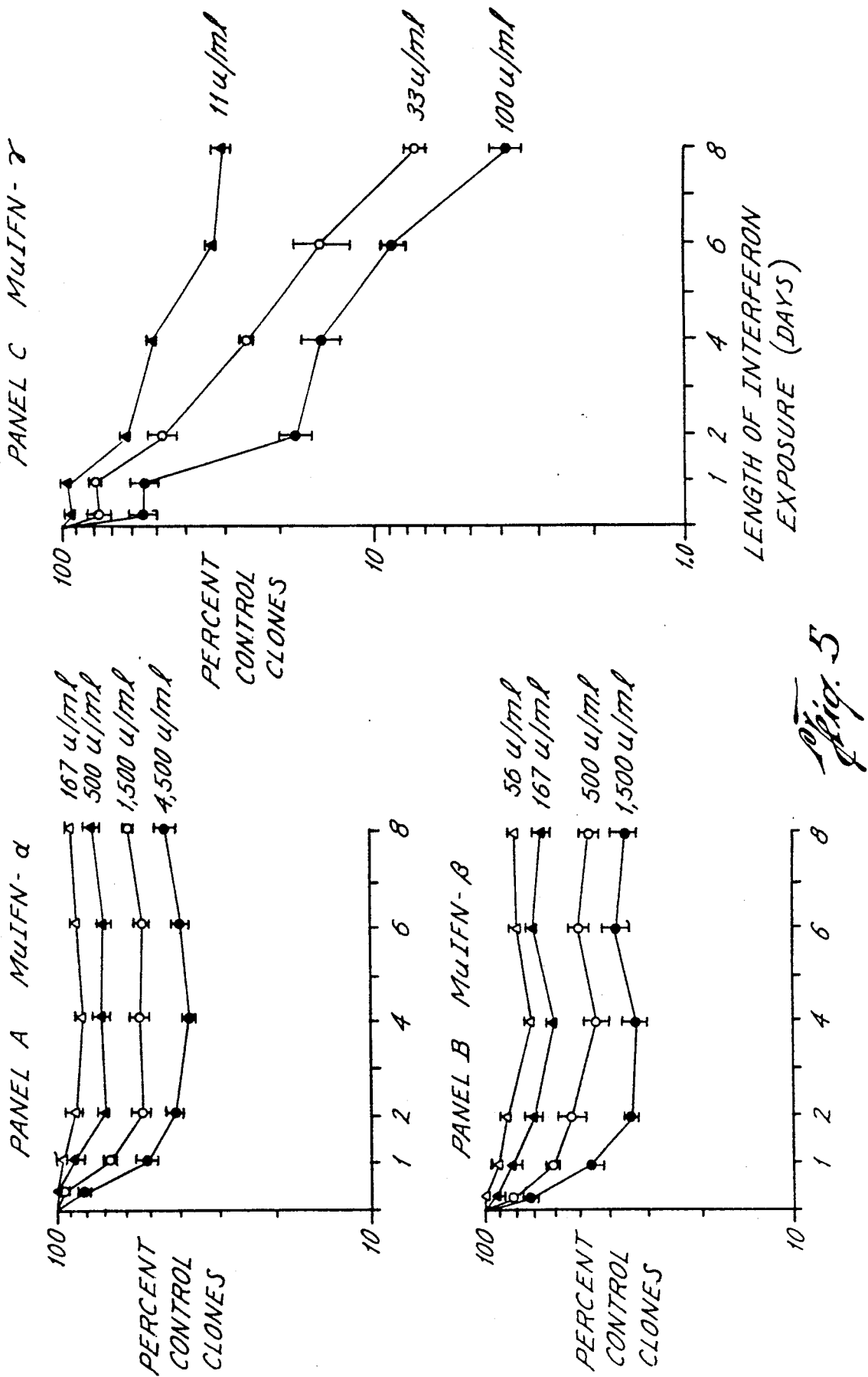
FIG. 5. Kinetics of development of murine interferon antiproliferative activity against B-16 melanoma cells. Subconfluent monolayers of murine B-16 melanoma cells were trypsinized and cloned in growth medium and in the presence of various concentrations of IFN-alpha, IFN-beta, and IFN-gamma. At the indicated times after plating, the plates were removed from the incubator. The interferon was gently removed and replaced with fresh growth medium. The plates were reincubated. Eight days after plating, the cells were stained with crystal violet and the clones were counted. Experiments were performed in quadruplicate. Cells cloned in growth medium had a 70% cloning efficiency. The results are plotted as percent of control clones versus the number of days of interferon treatment. Panel A, IFN-alpha; Panel B, IFN-beta; Panel C, IFN-gamma. Points, mean; bars, SE.

2. Kinetics of Development of MuIFN-alpha, MuIFN-beta, and MuIFN-gamma Antiproliferative Activities B-16 melanoma cells were cloned in the presence of growth medium or of varying concentrations of IFN-alpha, IFN-beta, and IFN-gamma. At various times after the initiation of cloning, the growth medium or interferons were removed and replaced with fresh growth medium. This procedure had little effect on clone development. When the clone counts from plates which were fluid changed after varying times of incubation were compared to those of plates which were not fluid changed, the variability from day to day was found to be no greater than the standard deviation of clone counts for replicate plates on any one day. FIG. 5 presents the results of a representative experiment. Panel A presents the effect of treatment with IFN-alpha for varying period of time. Over the initial two days, IFN-alpha's inhibitory effect on clone formation increased with increasing time of interferon treatment. However, after 2 to 4 days, no further inhibition of clone formation occurred. Thus, the maximal IFN-alpha antiproliferative effect was attained with as little as two days of IFN-alpha treatment.

Panel B presents the effect of treatment with MuIFN-beta for varying periods of time. The results with MuIFN-beta were essentially identical with those seen with MuIFN-alpha. This inhibitory effect on clone formation increased with time for the first two days and the maximal interferon effect was attained with about two days of IFN-beta treatment.

Panel C presents the effect of treatment with IFN-gamma for varying periods of time. The results with IFN-gamma are in marked contrast to those observed for IFN-alpha and IFN-beta. IFN-gamma's inhibitory effect on clone formation continued to increase with increasing time of interferon treatment over the whole time course of the experiment.

3. Effect of IFN-alpha and IFN-beta Stabilities on the Development of Resistance To examine the relative stabilities of the three interferon types, the kinetics experiments were repeated and the supernatant fluids (which were removed from the plates after varying times of incubation) were assayed for remaining interferon activity. As shown in Table 5, the activities of both IFN-alpha and IFN-beta were significantly decreased with increasing incubation time. After 2 days of incubation, IFN-alpha and IFN-beta titers had dropped to 49% and 70% of their initial values. With 8 days of incubation, their titers dropped to 16% and 37% of their initial values, respectively. IFN-gamma was relatively more stable, with 59% of the initial level of interferon remaining after 8 days of incubation. Thus, the data suggested that the loss of titer of IFN-alpha and IFN-beta might have contributed to the plateauing of their antiproliferative effects.

TABLE 5

Loss of Interferon Activity with Increasing Incubation Time

| Interferon | | % initial interferon remaining | | | |
|---|---|---|---|---|---|
| | | Day 1 | Day 2 | Day 4 | Day 8 |
| MuIFN-alpha | Exp. 1 | 63 | 43 | 29 | 17 |
| | Exp. 2 | 62 | 54 | 41 | 15 |
| | Average | 63 ± 0.5 | 49 ± 5.5 | 35 ± 6 | 16 ± 1 |
| MuIFN-beta | Exp. 1 | 94 | 58 | 39 | 27 |
| | Exp. 2 | 88 | 82 | 70 | 46 |
| | Average | 91 ± 3.0 | 70 ± 12 | 55 ± 16 | 37 ± 9.5 |
| MuIFN-gamma | Exp. 1 | 80 | 74 | 74 | 64 |
| | Exp. 2 | 76 | 81 | 67 | 54 |
| | Average | 78 ± 2.8 | 78 ± 4.9 | 71 ± 4.9 | 59 ± 7.1 |

To offset the possible effects of the loss the interferon titer with continued incubation at 37° C., the kinetics experiments were repeated except that the plates were fluid changed each day and replenished with either growth medium or the appropriate interferon. These experiments demonstrated that daily replacement of interferon produced results similar to those seen with the original experiments.

4. The Nature of the Resistant State

B-16 melanoma cells were cloned in the presence of growth medium, IFN-alpha or IFN-beta. After 10 days under cloning conditions, the cloned cells were trypsinized and growth for two days in monolayer culture. Cells cloned in growth medium were grown in the presence of growth medium. Cells cloned in the presence of interferon were split into two groups: One group of cells were grown in growth medium and the other group was grown in interferon. The cells were then recloned in the presence of growth medium, IFN-alpha, IFN-beta, or IFN-gamma. As shown in Table 6, cells which were cloned in growth medium were as sensitive to interferons upon recloning as cells which had never been cloned. Cells cloned in IFN-alpha or IFN-beta, maintained in the interferons, and recloned in the interferons were resistant to the antiproliferative activity of IFN-alpha and IFN-beta, though they retained their sensitivity of IFN-gamma. This was true even when cells cloned in IFN-alpha and IFN-beta were maintained in growth medium for 2 days and then recloned in the interferons. It is of interest to note that while the cells which were cloned and maintained in the presence of IFN-alpha or IFN-beta were insensitive to those interferons, they were more responsive to IFN-gamma than cells originally cloned in growth medium, IFN-alpha or IFN-beta.

TABLE 6

| Interferon Sensitivites of Cells Cloned in MuIFN-alpha and MuIFN-beta | | | | |
|---|---|---|---|---|
| Original Cloning Treatment (10 days) | Intermediate Treatment (2 days) | Second Cloning Treatment (% Control Clones + SD) | | |
| | | MuIFN-alpha (1500 U/ml) | MuIFN-beta (500 U/ml) | Mu-IFN-gamma (33 U/ml) |
| EMEM | EMEM | 64 + 6.4 | 59 + 4.8 | 15 + 3.6 |
| MuIFN-alpha | MuIFN-alpha | 97 + 4.0 | 98 + 3.0 | 4.5 + 0.4 |
| MuIFN-alpha | EMEM | 95 + 3.6 | 93 + 7.6 | 18 + 1.4 |
| MuIFN-beta | MuIFN-beta | 109 + 4.8 | 95 + 9.2 | 4.7 + 1.4 |
| MuIFN-beta | EMEM | 93 + 8.6 | 97 + 10 | 13 + 1.0 |

5. Stability of the Resistant State

The data shown above suggested that the resistance to IFN-alpha and IFN-beta's antiproliferative effect was stable for at least 2 days of incubation in growth medium. The stability of the resistant state was directly addressed in the following experiment. One set of cells were cloned in growth medium and maintained in culture in growth medium. A second set of cells were cloned in IFN-alpha and maintained in culture with IFN-alpha. A third set of cells were cloned in IFN-alpha and maintained in culture in growth medium. All 3 sets of cells were recloned at various intervals in the presence of growth medium, IFN-alpha, IFN-beta or IFN-gamma. The expected levels of inhibition for each of the types of interferon were determined from the interferon sensitivities of cells which had been initially cloned and maintained in the presence of growth medium. Complete resistance (100%) was defined as control levels of clones. The data indicated that cells cloned and maintained in the presence of IFN-alpha remained resistant to the antiproliferative activities of IFN-alpha and IFN-beta (approximately 100% resistance to the interferons). Further, cells cloned in the presence of IFN-alpha but maintained in the presence of growth medium gradually lost their resistance to IFN-alpha and IFN-beta with increasing time after removal of IFN-alpha. After 23 days of culture in growth medium, approximately 34% of the cells were resistant to the IFN-alpha and IFN-beta. The sensitivity of both groups of cells to IFN-gamma remained constant over the course of the experiment.

6. Extension of the Observations with the Murine System to the Human System

Figure 6:
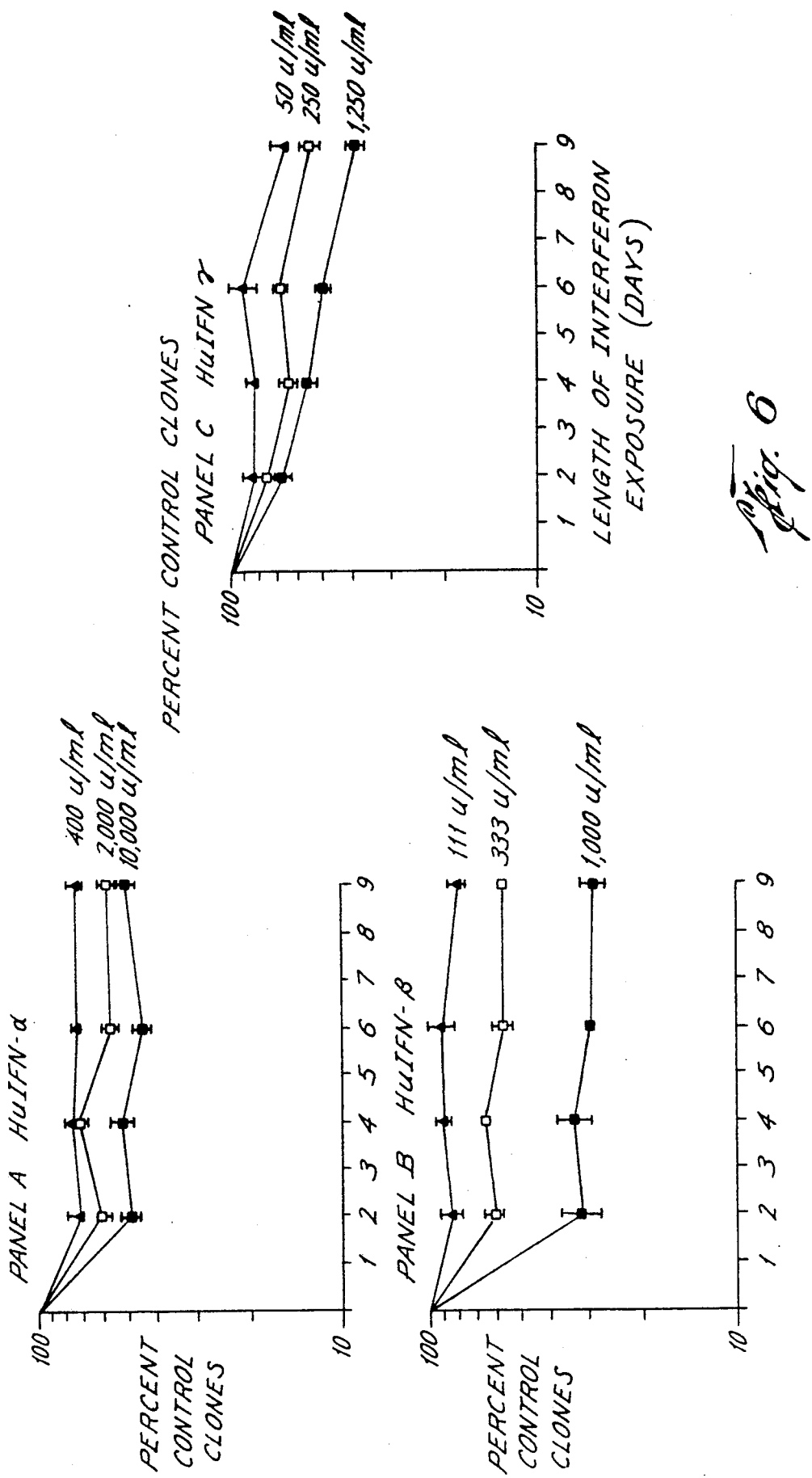
FIG. 6. Kinetics of development of human interferon antiproliferative activity against G-361 melanoma cells. Subconfluent monolayers of human G-361 melanoma cells were trypsinized and cloned in growth medium and in the presence of various concentrations of IFN-alpha, IFN-beta, and IFN-gamma. At the indicated times after plating, the plates were removed from the incubator. The interferon was gently removed and replaced with fresh growth medium. The plates were reincubated. Nine days after plating, the cells were stained with crystal violet and the clones were counted. Experiments were performed in quadruplicate. Cells cloned in growth medium had a 73% cloning efficiency. The results are plotted as percent of control clones versus the number of days of interferon treatment. Panel A, IFN-alpha, Panel B, IFN-beta, Panel C, IFN-gamma. Points mean; bars, SE.

Human G-361 melanoma cells were cloned in the presence of growth medium or of varying concentrations of HuIFN-alpha, HuIFN-beta, and HuIFN-gamma, exactly as described for murine B-16 melanoma cells. At various times after the initiation of cloning, the growth medium or interferons were removed and replaced with fresh growth medium. FIG. 6 presents the results of a representative experiment. Panels A and B presents the effect of treatment with IFN-alpha and IFN-beta, respectively. The data show that over the initial two days, IFN-alpha and IFN-beta's inhibitory effects on clone formation increased with increasing time of interferon treatment. In parallel with the observations with the murine system, the maximal interferon effect was attained with as little as two days of IFN-alpha and IFN-beta treatment.

Panel C presents the effect of treatment with IFN-gamma. Again, in parallel with the observations with the murine system, the results with IFN-gamma are in marked contrast to those observed for IFN-alpha and IFN-beta. IFN-gamma inhibitory effect on clone formation increased with increasing time of interferon treatment over the whole time course of the experiment.

The foregoing examples indicate the usefulness of employing fairly rigid treatment protocols for IFN therapy. In the clinical setting it is suggested that IFN-gamma therapy should be used in combination with IFN-alpha nd/or beta therapy in order to avoid the development of the resistant state associated with IFN-alpha/beta therapy alone. The reasons for IFN-gamma effect in eliminating the resistant state is unknown, however, the foregoing results conclusively demonstrate its utility in this respect. It is suggested, therefore, that IFN-gamma therapy be administered either concurrently with IFN-alpha and/or beta therapy, or more preferably, be administered in an alternating fashion as described above.

While combination and sequential treatment regimens have been employed in various other cancer chemotherapeutic settings, such use has always been predicated on an appreciation of complementary mechanisms of action of the combined or sequentially employed drugs. In the present instance, the results were quite surprising and unexpected in that no mechanism of action per se has been determined for IFN activity.

Thus, there is no basis for predicting that such complementation would occur, prior to the present invention.

E. Identification and Removal of an Inhibitor of IFN-gamma Activity

Numerous studies have indicated the presence of an IFN-gamma inhibitor in both naturally isolated and recombinant-DNA-derived IFN-gamma preparations (see, e.g., Lefkowitz, et al. (1985), *Jrnl. Interferon Res.*, 5: 85–110 (two articles), incorporated herein by reference). These studies have shown that this inhibitory activity is exerted in almost a dose-dependent fashion, that is, as the dose of IFN-gamma is increased, the inhibitory action of the inhibitor is also increased. It is speculated that the presence of this inhibitor greatly reduces the overall efficacy of IFN-gamma in the clinical setting. The present disclosure details a method whereby IFN-gamma-containing preparations may be treated to remove this inhibitory activity.

In accordance with this method, IFN-gamma containing preparations, however derived, whether from murine or human, or natural or recombinant sources, are first brought to a convenient concentration using any buffer in which they are known to be stable. It is believed that the IFN-gamma concentration is not crucial, nor is the particular starting buffer. However, the present inventors have found that the treatment may conveniently be performed in 10mm Tris at neutral pH, with IFN-gamma concentrations between 1 and 10,000 units/ml being optimal.

This IFN-gamma preparation is then reduced with a reducing agent to reduce disulfide-containing moieties to sulfhydryl moieties. Virtually any reducing agent capable of reducing these structures may be employed so long as such agent is not so strong as to reduce protein structures other than disulfide moieties. Agents which are believed to be particularly useful in this respect include, but are not limited to, dithiothreitol, and mercaptoethanol, sodium borohydride, iodate, glutathione. In a preferred embodiment, the reducing agent dithiothreitol (DTT) is employed at a final concentration of approximately 30 to 40 mM for 1 to 3 hours with the most preferred conditions being a final concentration of 32 mM DTT and a reaction time of 2 hours. The temperature at which the reaction is performed has not been found to be crucial and may be performed at any temperature at which the IFN-gamma itself is stable. The temperature may conveniently be maintained at ambient temperatures.

Following disulfide reduction, the reduced preparation is treated with an acylating agent to acylate the sulfhydryl moieties and thereby inhibit the reformation of disulfide bonds in the preparation. As with the reducing agent, the particular acylating agent is not believed to be particularly crucial and numerous such agents may be so employed, including but not limited to, alpha keto alkyl halides and their corresponding amides. In a preferred embodiment the acylating agent is an acetylating agent, for example, iodoacetate. Accordingly, the reduced preparation is brought to between about 70 and about 100 mM of the selected acylating agent. Again, the time which is required to achieve acylation of the sulfhydryl moieties does not appear to be particularly crucial nor does the concentration of the acylator. However, where particularly high concentrations of IFN-gamma are employed, as those of skill in the art will appreciate, higher concentrations of the acylator should be employed in that this reactant may be used up during the course of the acylation reaction. Moreover, although at IFN-gamma concentrations of approximately 5000 units/ml, a 20 minute treatment with the acylator is quite sufficient, longer reaction times may be needed for higher IFN-gamma concentrations.

The reaction may most conveniently be terminated through a second addition of reducing agent. However, any method which removes the reactants from the IFN-gamma preparation may be employed, for example, dialysis of the treated preparation in a suitable dialysis membrane. In a preferred embodiment, the acylated preparation is brought to between about 250 and about 350 mM 2-mercaptoethanol, to stop the reactivity of the acylator. Higher concentrations may be indicated where higher concentrations of the acylator have been employed. Whether the foregoing manner of termination is employed or not, the reaction mixture should preferably be dialyzed to remove the reactants from the preparation and/or achieve a suitable ionic environment for clinical utilization of the treated IFN-gamma.

Treatment of IFN-gamma preparations in the foregoing manner serves to permanently remove the IFN-gamma-inhibitory activity as exemplified by the following example.

EXAMPLE 8

Removal of IFN-gamma Inhibitor from IFN-gamma preparations

Natural human IFN-gamma, isolated as described above, was brought to approximately 5000 units/ml in 10 mM Tris, pH 7.4 and 32 mM DTT, using a 1 M stock solution of DTT through which nitrogen had been bubbled to remove dissolved oxygen. This mixture was allowed to stand at ambient temperature for approximately 2 hours, and then brought to 81 mM in iodoacetic acid, using a 1 M stock solution of iodoacetic acid. The acylation was stopped after 20 minutes at ambient temperature by the addition 2-mercaptoethanol. The solution was brought to 296 mM in 2-mercaptoethanol, allowed to sit at ambient temperature for 1 hour and then it was dialyzed against growth medium.

Figure 7:
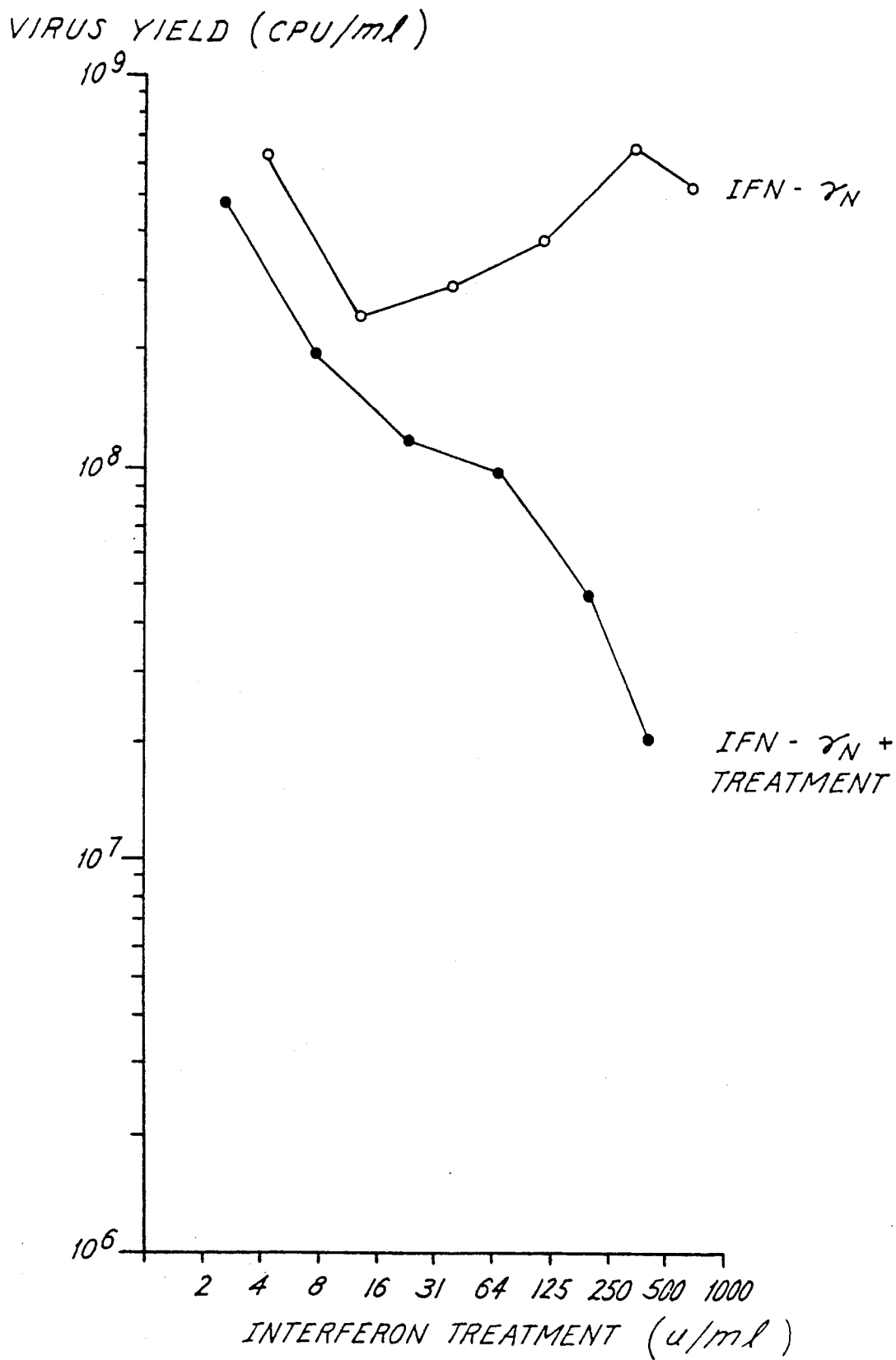
FIG. 7. Effect of treatment to remove inhibitor from IFN-gamma preparations on the antiviral activities of IFN-gamma. Confluent monolayers of B-16 melanoma cells were plated at a concentration of approximately $10^6$ cells/dish. The monolayers were split into groups and incubated with fresh growth medium, or serial dilutions of either untreated IFN-gamma (○) or treated IFN-gamma (●) in fresh growth medium. The monolayers were then challenged with Mengo virus (Franklin isolate) at a multiplicity of infection of approximately 10 PFU/cell. After a 45-minute incubation for virus adsorption, the monolayers were overlaid with growth medium. Progeny virus were harvested 24 hours post infection. Virus titers were determined by plaque assay.

The treated IFN-gamma was then tested in the virus yield assay as described above and the results demonstrated in FIG. 7. As depicted therein, the treated IFN-gamma preparation was able to achieve a virus yield reduction from approximately $4.8 \times 10^9$ PFU/ml (at an IFN-gamma concentration of about 2 units/ml) to about $2 \times 10^8$ (at about 400 units of treated IFN-gamma/ml.) At the later concentration of IFN-gamma, the non-treated IFN-gamma preparation demonstrated virtually no reduction in virus yield over control.

What is claimed is:

1. A method of enhancing the effectiveness of an interferon gamma preparation comprising the steps of:
   (a) providing an aqueous preparation which includes interferon gamma;
   (b) treating the aqueous preparation with a reducing agent to reduce disulfide moieties to sulfhydryl moieties to produce a reduced preparation; and
   (c) treating the reduced preparation with an acylating agent to acylate the reduced sulfhydryl moieties and thereby inhibit the formation of disulfide bonds in the preparation wherein said acylated interferon has enhanced antiviral activity as measured by a virus yield assay.

2. The method of claim 1 wherein the reducing agent is selected from the group consisting of dithiothreitol and 2-mercaptoethanol.

3. The method of claim 1 wherein the acylating agent is iodoacetate.

4. The method of claim 1 wherein the reducing agent is dithiothreitol and the acylating agent is iodoacetate.

5. The method of claim 2 wherein the selected reducing agent is dithiothreitol.

6. The method of claim 2 wherein the selected reducing agent is 2-mercaptoethanol.

* * * * *